United States Patent [19]

Mallet et al.

[11] Patent Number: 5,648,259

[45] Date of Patent: Jul. 15, 1997

[54] POLYPEPTIDES HAVING NMDA RECEPTOR ACTIVITY, NUCLEIC ACIDS ENCODING THOSE POLYPEPTIDES AND APPLICATIONS

[75] Inventors: Jacques Mallet, Paris; Tania Smirnova, Sceaux, both of France

[73] Assignee: Rhone-Poulenc Rorer S.A., Antony, France

[21] Appl. No.: 356,397

[22] PCT Filed: Jun. 11, 1993

[86] PCT No.: PCT/FR93/00557

§ 371 Date: Jan. 27, 1995

§ 102(e) Date: Jan. 27, 1995

[87] PCT Pub. No.: WO93/25679

PCT Pub. Date: Dec. 23, 1993

[30] Foreign Application Priority Data

Jun. 15, 1992 [FR] France ................................ 92 07177

[51] Int. Cl.⁶ .......................... C07K 14/705; C12N 5/10; C12N 15/12

[52] U.S. Cl. .................. 435/252.3; 435/64.1; 530/350; 536/23.5

[58] Field of Search ........................ 435/64.1, 7.2, 435/252.3; 530/350; 536/23.5

[56] References Cited

PUBLICATIONS

Inoue et al., *J. of Biol. Chem.* 267(15):10613–10618, 25 May 1992.

J. Biol. Chem. 267(15): 10613–19, May 25, 1992 Cloning and sequence analysis of cDNA for a neuronal cell membrane antigen, HPC–1'.

*Primary Examiner*—John Ulm
*Attorney, Agent, or Firm*—Julie K. Smith; Martin F. Savitzky

[57] ABSTRACT

The present invention concerns novel polypeptides having NMDA receptor activity and genetic material permitting their expression. It also concerns a method for demonstrating and isolating ligands and/or modulators of the activity of these polypeptides and their utilization as drugs.

16 Claims, 5 Drawing Sheets

```
            10                  30                    50
  1 GTTCTTTGAACAGGTGGAAGAGATCCGAGGCTGCATTGAGAAACTGTCGGAGGATGTGGA
  1  F  F  E  Q  V  E  E  I  R  G  C  I  E  K  L  S  E  D  V  E 70                  90                   110
 61 GCAGGTGAAAAAACAGCATAGCGCCATCCTGGCCGCACCCAACCCAGATGAGAAGACCAA
 21  Q  V  K  K  Q  H  S  A  I  L  A  A  P  N  P  D  E  K  T  K 130                 150                   170
121 ACAGGAGCTGGAGGATCTCACTGCAGACATCAAGAAGACGGCCAACAAGGTTCGGTCCAA
 41  Q  E  L  E  D  L  T  A  D  I  K  K  T  A  N  K  V  R  S  K 190                 210                   230
181 ATTGAAAGCGATCGAGCAAAGCATTGAACAGGAGGAGGGGCTGAACCGTTCCTCCGCGGA
 61  L  K  A  I  E  Q  S  I  E  Q  E  E  G  L  N  R  S  S  A  D 250                 270                   290
241 CCTGCGCATCCGCAAGACCCAGCACTCCACACTGTCCCGGAAGTTCGTGGAGGTAATGAC
 81  L  R  I  R  K  T  Q  H  S  T  L  S  R  K  F  V  E  V  M  T 310                 330                   350
301 CGAATATAACGCGACCCAGTCCAAGTACCGGGACCGCTGCAAGGACCGGATCCAGCGGCA
101  E  Y  N  A  T  Q  S  K  Y  R  D  R  C  K  D  R  I  Q  R  Q 370                 390                   410
361 ACTGGAGATCACTGGAAGGACCACCACCAACGAAGAACTGGAAGACATGCTGGAGAGCGG
121  L  E  I  T  G  R  T  T  T  N  E  E  L  E  D  M  L  E  S  G 430                 450                   470
421 GAAGCTGGCCATCTTCACAGATGACATGAAAATGGACTCACAGATGACGAAACAGGC
141  K  L  A  I  F  T  D  D  I  K  M  D  S  Q  M  T  K  Q
```

POLYPEPTIDES HAVING NMDA RECEPTOR ACTIVITY, NUCLEIC ACIDS ENCODING THOSE POLYPEPTIDES AND APPLICATIONS

The present invention relates to new polypeptides and to the genetic material permitting their expression. More especially, it relates to new polypeptides having NMDA receptor activity.

Glutamic acid (glutamate) is a so-called excitatory amino acid, whose activity manifests itself in its interaction with specific receptors. Among these receptors, a subtype, designated NMDA (N-methyl-D-aspartate) receptors, appears to be implicated in the central nervous system of mammals, in many processes such as neuronal plasticity, long-term potentiation and also neuronal death or certain degenerative disorders. Pharmacological and molecular biology studies have recently made it possible to demonstrate and clone rat NMDA receptors, the receptor NMDAR1 [Moriyoshi et al., Nature 354 (1991) 31] and the receptor NMDAR2 [Monyer et al., Science 256 (1992) 12], and a mouse NMDA receptor [Yamazaki et al., Febs Lett. 300 (1992) 39].

The present invention is the outcome of the demonstration of new polypeptides having NMDA receptor activity. While belonging to the family of receptors associated with ion channels, these new polypeptides differ from the NMDA receptors already described from both a structural standpoint and a pharmacological standpoint. In particular, the receptors in question are of presynaptic origin, involved, in particular, in long-term potentiation (LTP).

More especially, the invention is the outcome of the isolation and characterization of new polypeptides, designated GR33, and also of the genetic material permitting their expression or identification. The invention also lies in the preparation of probes and of recombinant cells enabling the GR33 polypeptides to be exploited in diagnosis and the development of new active molecules.

A first subject of the invention hence lies in polypeptides comprising all or part of the peptide sequence SEQ ID No. 2 or of a derivative of the latter.

For the purposes of the present invention, the term derived denotes any molecule obtained by modification, of a genetic and/or chemical nature, of the peptide sequence SEQ ID No. 2. Modification of a genetic and/or chemical nature is understood to mean any mutation, substitution, deletion, addition and/or modification of one or more residues. Such derivatives may be generated for different purposes, such as, in particular, that of increasing the affinity of the peptide for its ligand(s), that of improving its levels of production, that of increasing its resistance to proteases, that of increasing and/or modifying its activity or that of endowing it with new pharmacokinetic and/or biological properties. Among derivatives resulting from an addition, chimeric polypeptides containing an additional heterologous portion attached at one end may, for example, be mentioned. The term derivative also comprises polypeptides homologous with the polypeptide SEQ ID No. 2, originating from other cell sources, and in particular from cells of human origin or of other organisms and possessing an activity of the same type. Such homologous polypeptides may be obtained by hybridization and/or PCR experiments, as described in the examples.

Preferably, the polypeptides of the invention are polypeptides possessing the capacity to bind glutamate. Still more preferably, they are polypeptides having NMDA receptor activity. Still according to a preferred embodiment, the polypeptides of the invention are capable of being recognized by antibodies which recognize the complete peptide sequence SEQ ID No. 2.

A particular embodiment of the invention is represented by the polypeptide GR33 comprising the whole peptide sequence SEQ ID No. 2. As shown in the examples, this polypeptide may be expressed in Xenopus eggs to form a functional glutamate receptor displaying all the pharmacological characteristics of an NMDA receptor:

the presence of 100 µM NMDA induces an inward current;

the absence of glycine from the medium inhibits the response to NMDA almost completely;

the responses to NMDA are reduced in the presence of competitive antagonists such as AP5 (D-2-amino-5-phosphonovaleric acid) or AP7 (D-2-amino-7-phosphonoheptanoic acid);

the NMDA concentration giving 50% of the maximum response ($ED_{50}$) is approximately 10 µM, corresponding to the values determined in the cases of the receptor NMDAR1;

among the other excitatory amino acids tested (glutamate, kainate, quisqualate, homocysteate), glutamate and homocysteate are those which induce the strongest responses.

Moreover, the results obtained show that the GR33 polypeptide comprising the whole peptide sequence SEQ ID No. 2 displays distinctive features relative to the other, known NMDA receptors. In particular, magnesium has only a partial inhibitory effect (30–70%) whereas it completely inhibits the activity of known NMDA receptors, and calcium has an inhibitory effect whereas it stimulates the activity of the NMDA receptors described. Furthermore, these distinctive pharmacological features are associated with distinctive structural features. In effect, the GR33 polypeptide SEQ ID No. 2, which comprises 288 amino acids and possesses a molecular weight of approximately 33 kDa, contains only a single hydrophobic domain (20 to 23 uncharged residues on the C-terminal side). This polypeptide also contains 2 potential glycosylation sites (Asn 115 and 134) and 4 cysteines which might be involved in the formation of secondary structures.

Figure 1:
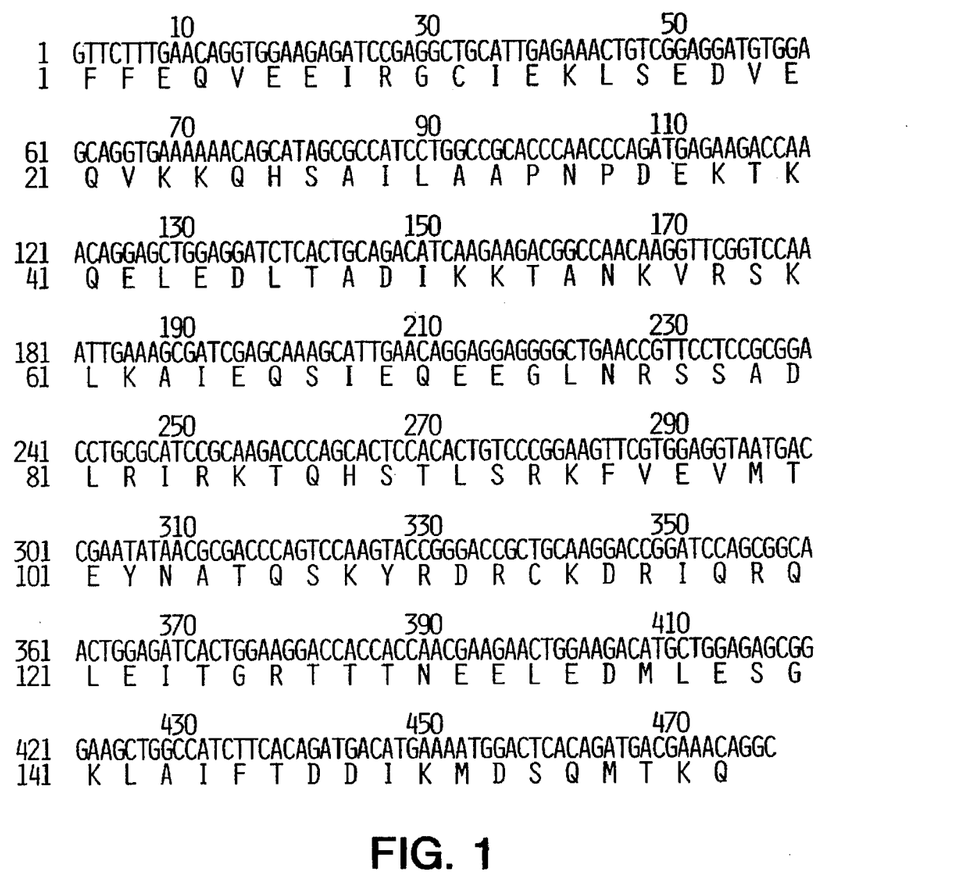
FIG. 1: Fragment of the nucleotide (SEQ ID NO: 3) and peptide (SEQ ID NO: 4) sequence of the human GR33 receptor.

Another particular embodiment of the invention is represented by a polypeptide comprising the sequence presented in FIG. 1. This sequence corresponds to a fragment of a receptor homologous with the polypeptide SEQ ID No. 2, obtained from a human brain bank.

The polypeptides of the invention may be obtained by expression of a nucleotide sequence as described below in a cell host, by chemical synthesis on the basis of the given sequences SEQ ID No. 2 and FIG. 1 using techniques known to a person skilled in the art (solid- or liquid-phase peptide synthesis, and the like), or by a combination of these techniques.

In what follows, the polypeptides of the invention as defined above are designated GR33 polypeptides.

The subject of the present invention is also any nucleotide sequence coding for a GR33 polypeptide. More preferably, such a sequence is chosen from:

(a) all or part of the nucleotide sequence SEQ ID No. 1 or of its complementary strand, (b) any sequence hybridizing with a sequence (a) and coding for a polypeptide as defined above, and (c) the sequences derived from the sequences (a) and (b) as a result of the degeneracy of the genetic code.

The different nucleotide sequences of the invention can be of artificial origin or otherwise. They can be genomic, cDNA or RNA sequences, hybrid sequences or synthetic or semi-synthetic sequences. These sequences may be obtained, for example, by screening DNA libraries (cDNA library, genomic DNA library) by means of probes devised on the basis of the sequence SEQ ID No. 1. Such libraries may be prepared from cells of different origins by standard techniques of molecular biology known to a person skilled in the art. The nucleotide sequences of the invention may also be prepared by chemical synthesis, in particular according to the phosphoramidite method, or alternatively by mixed methods including the chemical or enzymatic modification of sequences obtained by screening libraries.

As an example of sequences hybridizing with a sequence (a) and coding for a polypeptide according to the invention, the sequence presented in FIG. 1 may be mentioned. Another example of a homologous sequence is represented by the human genomic clone described in FIG. 2, also isolated by hybridization.

The nucleotide sequences of the invention may be used for the production of GR33 polypeptides as defined above. In this case, the portion coding for the said polypeptide is generally placed under the control of signals permitting its expression in a cell host. The choice of these signals (promoters, terminators, and the like) can vary in accordance with the cell host used. To this end, the nucleotide sequences of the invention can form part of a vector, which can be an autonomously replicating or integrative vector. More especially, autonomously replicating vectors may be prepared using sequences which replicate autonomously in the chosen host. As regards integrative vectors, these may be prepared, for example, using sequences homologous with certain regions of the host's genome, permitting integration of the vector by homologous recombination. The cell hosts which are usable for the production of the GR33 polypeptides of the invention by the recombinant method are either eukaryotic or prokaryotic hosts. Among suitable eukaryotic hosts, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127 cells, Xenopus eggs, and the like, may be mentioned. Among fungi, Aspergillus ssp. or Trichoderma ssp. may be mentioned more especially. As prokaryotic hosts, it is preferable to use the following bacteria: *E. coil*, Bacillus or Streptomyces.

The nucleotide sequences of the present invention are also usable in the pharmaceutical field, either for the production of sense or antisense sequences which may be used in the context of a gene therapy, or else for the production of probes permitting the detection, by hybridization experiments, of the expression of NMDA receptors in biological samples, and the demonstration of genetic abnormalities (polymorphism, mutations) or of aberrant expressions.

Inhibition of the expression of certain genes by antisense oligonucleotides has proved to be a promising strategy in controlling the activity of a gene. Antisense oligonucleotides are small-sized oligonucleotides complementary to the coding strand of a given gene and, as a result, capable of hybridizing specifically with the transcribed mRNA inhibiting its translation into protein. A subject of the invention is thus antisense oligonucleotides capable of at least partially inhibiting the production of GR33 polypeptides. Such oligonucleotides can consist of all or part of the nucleotide sequences defined above. They are generally sequences or fragments of sequences complementary to sequences coding for peptides of the invention. Such oligonucleotides may be obtained from the sequence SEQ ID No. 1 or the sequence given in FIG. 1, by fragmentation, and the like, or by chemical synthesis. The sequences of the invention may also be used in gene therapy, incorporated in vectors, in particular viral vectors (adenoviruses, retroviruses, adeno-associated viruses, and the like).

As stated above, the invention also makes it possible to produce nucleotide probes, synthetic or otherwise, capable of hydriding with the nucleotide sequences defined above which code for GR33 polypeptides of the invention, or with the corresponding mRNAs. Such probes may be used in vitro as a diagnostic tool for detecting the expression of a GR33 glutamate receptor, or alternatively for demonstrating genetic abnormalities (incorrect splicing, polymorphism, point mutations, and the like). In view of the numerous activities of the glutamate receptors, the probes of the invention may thus enable neurological, cardiovascular or psychiatric disorders to be identified as being associated with GR33 receptors. These probes may also be used for demonstrating and isolating homologous nucleic acid sequences coding for GR33 polypeptides as defined above, from other cell sources and preferably from cells of human origin, as illustrated in the examples. The probes of the invention generally contain at least 10 bases, and they can contain as much as the whole of the sequence presented as SEQ ID No. 1 or in FIG. 1, or of their complementary strand. Preferably, these probes are labelled prior to their use. For this purpose, different techniques known to a person skilled in the art may be employed (radioactive or enzymatic labelling, and the like). The hybridization conditions under which these probes may be used are mentioned in the general cloning techniques below, as well as in the examples.

Another subject of the invention lies in polyclonal or monoclonal antibodies or antibody fragments directed against a GR33 polypetide as defined above. Such antibodies may be generated by methods known to a person skilled in the art, bearing in mind the teachings given in the present application. In particular, these antibodies may be prepared by (1) immunizing an animal against the GR33 polypeptide whose sequence is given as SEQ ID No. 2 or in FIG. 1, or any fragment or derivative of these, (2) withdrawing blood, and (3) isolating the antibodies. These antibodies may also be generated by preparing hybridomas according to techniques known to a person skilled in the art.

The antibodies thereby obtained may be used, in particular, for demonstrating and isolating homologous nucleic acid sequences coding for GR33 polypeptides as defined above, from other cell sources and preferably from cells of human origin, as illustrated in the examples. They may also be used for demonstrating and isolating GR33 polypeptides.

Another subject of the invention relates to recombinant cells capable of expressing at their surface one or more GR33 polypeptides. These cells may be obtained by introducing a nucleotide sequence as defined above, coding for a polypeptide of the invention, and then culturing the said cells under conditions for expression of the said sequence.

The recombinant cells according to the invention can be either eukaryotic or prokaryotic cells. Among suitable eukaryotic cells, animal cells, yeasts or fungi may be mentioned. In particular, as regards yeasts, yeasts of the genus Saccharomyces, Kluyveromyces, Pichia, Schwanniomyces, or Hansenula may be mentioned. As regards animal cells, COS, CHO, C127 cells, Xenopus eggs, and the like, may be mentioned. Among fungi, *Aspergillus ssp.* or *Trichoderma ssp.* may be mentioned more especially. As prokaryotic cells, it is preferable to use the following bacteria: *E. coli*, Bacillus or Streptomyces. The cells thereby obtained may be used to measure the ability of different molecules to behave as a ligand or as a modulator of the polypeptides of the invention. More especially, they may thus be used in a method for demonstrating and isolating ligands or modulators of the polypeptides of the invention, and more preferably glutamate agonists and antagonists.

Another subject of the invention hence relates to a method for demonstrating and/or isolating ligands of the polypeptides of the invention, according to which the following steps are carried out:

a molecule or a mixture containing different molecules, which are possibly unidentified, is brought into contact with a recombinant cell as described above, expressing at its surface a polypeptide of the invention, or with a membrane preparation of such a cell, under conditions permitting interaction between the said polypeptide of the invention and the said molecule should the latter possess an affinity for the said polypeptide, and the molecules bound to the said polypeptide of the invention are detected and/or isolated.

In a particular embodiment, this method of the invention is suitable for demonstrating and/or isolating glutamate agonists and antagonists for the polypeptides of the invention.

Another subject of the invention relates to a method demonstrating and/or isolating modulators of the polypeptides of the invention, according to which the following steps are carried out:

a molecule or a mixture containing different molecules, which are possibly unidentified, is brought into contact with a recombinant cell as described above, expressing at its surface a polypeptide of the invention, or with a membrane preparation of such a cell, in the presence of glutamate, under conditions permitting interaction between the said polypeptide of the invention and glutamate, and the molecules capable of modulating the activity of glutamate with respect to the said polypeptide of the invention are detected and/or isolated.

Another subject of the invention relates to the use of a ligand or modulator identified and/or obtained according to the method described above, as a medicinal product. Such ligands or modulators can, in effect, enable certain neurological, cardiovascular or psychiatric disorders associated with GR33 receptors to be treated.

The invention also relates to any medicinal product comprising as active principle at least one molecule which acts on a peptide of the invention. Preferably, the molecule is a ligand or a modulator identified and/or isolated according to the method described above.

Other advantages of the present invention will become apparent on reading the examples which follow, which are to be considered as illustrative and non-limiting.

LEGEND TO THE FIGURES

SEQ ID NOs: 1 and 2: Nucleotide and peptide sequences of the rat GR33 receptor.

GENERAL CLONING TECHNIQUES

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extractions with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley and Sons, New York 1987].

Restriction enzymes were supplied by New England Biolabs (Biolabs), Bethesda Research Laboratories (BRL) or, Amersham, and are used according to the suppliers' recommendations.

Plasmids of the pBR322, pUC, λgt11 and pGEX type and phages of the M13 series are of commercial origin.

For ligation, the DNA fragments are separated according to size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling-in of 5' protruding ends is performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides is performed according to the method developed by Taylor et al. [Nucleic Acids Res. 13 (1985) 8749–8764] using the kit distributed by Amersham.

The enzymatic amplification of DNA fragments by the so-called PCR [Polymerase-catalyzed Chain Reaction, Saiki R. K. et al., Science 230 (1985) 1350–1354; Mullis K. B. and Faloona F. A., Meth. Enzym. 155 (1987) 335–350] technique is performed using a "DNA thermal cycler" (Perkin Elmer Cetus) according to the manufacturer's specifications.

Verification of the nucleotide sequences is performed by the method developed by Sanger et al. [Proc. Natl. Acad. Sci. USA, 74 (1977) 5463–5467] using the kit distributed by Amersham.

For the hybridization experiments, the normal conditions of stringency are generally as follows: hybridization: 3×SCC in the presence of 5×Denhart's at 65° C.; washing: 0.5×SSC at 65° C.

1. Cloning of the cDNA H500 of FIG. 1

This example describes the cloning of an approximately 500-bp cDNA from human brain, coding for a portion of GR33 polypeptide. This cDNA was obtained by screening a human brain library by means of antibodies directed against glutamate-binding proteins.

1.1 Preparation of Purified Glutamate-Binding Proteins.

Synaptosomal membranes were prepared according to the technique described by Michaelis et al. [J. Neurochem. 42 (1984) 397] and solubilized in the presence of sodium deoxycholate. The membranes thus solubilized were then subjected to affinity chromatography on a glutamate column. The glutamate-binding proteins were eluted with 1M NaCl solution and dialysed against Tris-HCl buffer in the presence of 0.05% of sodium deoxycholate.

1.2. Production of Polyclonal Antibodies.

Polyclonal antibodies directed against the glutamate-binding proteins obtained above were prepared in mice. For this purpose, BALB/C mice were immunized with 50–100 µg of the glutamate-binding proteins obtained above, in the presence of Freund's complete adjuvant. Subsequent injections (every 8 to 10 days) were carried out with 50 µg of glutamate-binding proteins, but without Freund's complete adjuvant. After 5 injections, the sera were collected and stored frozen.

1.3. Screening of a Human Brain Library.

The antibodies prepared above were used to screen a human brain library produced in the vector lambda λgt11 (Clontech). Two million clones of this library were screened immunologically in this way, according to the technique described by Sambrook, Fritsch and Maniatis (see general cloning techniques). The positive clones identified were then purified to homogeneity by several successive screening steps. From these clones, an approximately 500-bp cDNA was obtained and sequenced on both strands. The sequence of this cDNA, designated H500, is presented in FIG. 1. No particular homology was found between this sequence and those available in the libraries.

2. Cloning of the cDNA Coding for the GR33 Polypeptide SEQ ID No.2

This example describes the cloning of an approximately 1.7-kb cDNA from rat brain, coding for the GR33 polypeptide SEQ ID No. 2. This cDNA was obtained by screening a rat brain library using radio-labelled cDNA H500 as probe.

The cDNA coding for the GR33 polypeptide SEQ ID No. 2 was obtained by screening a rat brain library constructed in the vector lambda ZAP (Stratagene). This library was screened with cDNA H500 previously labelled with $^{32}$P by the "random priming" technique [Feinberg and Vogelstein, Analytical Biochemistry 132 (1984) 6}]. Hybridization was carried out under the following highly stringent conditions: hybridization at 65° C., 3–4×SSC, 5×Denhardt's, rinsing at 65° C., 0.1×SSC, 1% SDS. Approximately 1 million clones of the library were analysed in this way. One positive clone was isolated and purified. The plasmid carried by this clone was excised from the lambda ZAP DNA by means of a helper phage (Stratagene), and the 1.7-kb cDNA carried by this plasmid was sequenced on both strands. A portion of the sequence thereby obtained is presented in SEQ ID No. 1.

3. In Vitro Translation of the 1.7-kb cDNA

Figure 3:
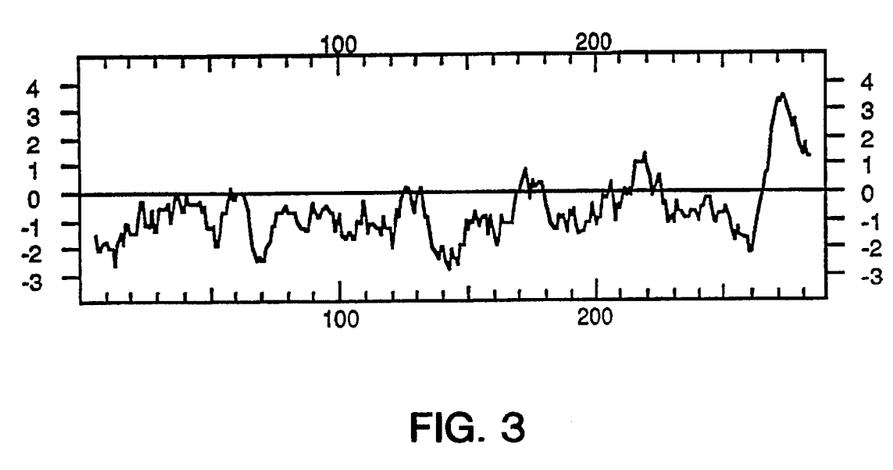
FIG. 3: Hydrophobicity profile of the GR33 polypeptide of 288 amino acids.

The 1.7-kb cDNA isolated above was translated in vitro in the rabbit reticulocyte system (Promega). This enabled an expressed protein having a molecular weight of approximately 35 kDA to be demonstrated. The protein deduced from the sequence SEQ ID No. 1 possesses a theoretical weight of 33.2 kDa. The hydrophobicity profile of the resulting protein of 288 amino acids was analysed according to the programme of Kyte and Doolittle [J. Molec. Biol. 157 (1982) 105]. The profile obtained is presented in FIG. 3. It indicates that the GR33 polypeptide comprising the whole sequence SEQ ID No. 2 possesses only one hydrophobic domain.

4. Expression of the GR33 Polypeptide SEQ ID No. 2 in Xenopus Eggs, and Pharmacological and Electrophysiological Study The cDNA fragment isolated in Example 2 was transcribed into mRNA and microinjected into Xenopus eggs. The microinjected eggs thereby obtained were then tested for their capacity to bind certain labelled NMDA receptor ligands, or for their behaviour with respect to modulators of NMDA receptors.

4.1. In Vitro Transcription

The plasmid containing the 1.7-kb cDNA coding for the GR33 polypeptide SEQ ID No. 2 was linearized in the presence of the enzyme SmaI, and then subjected to a transcription step in the presence of phage T7 RNA polymerase. Transcription was performed using the Stratagene Kit according to the manufacturer's recommendations.

4.2. Microinjection

The synthetic RNA obtained above, dissolved in sterile water, was used (5 ng) for injection into mature Xenopus eggs (stages V and VI) in a volume of 50 nl. The eggs were then maintained for 3 days at 19° C. in multi well plates in a Barth medium supplemented with antibiotics (Miledi and Sumikawa, Biomed. Res. 3 (1982) 390).

4.3. Pharmacological and Electrophysiological Study

Figure 4:
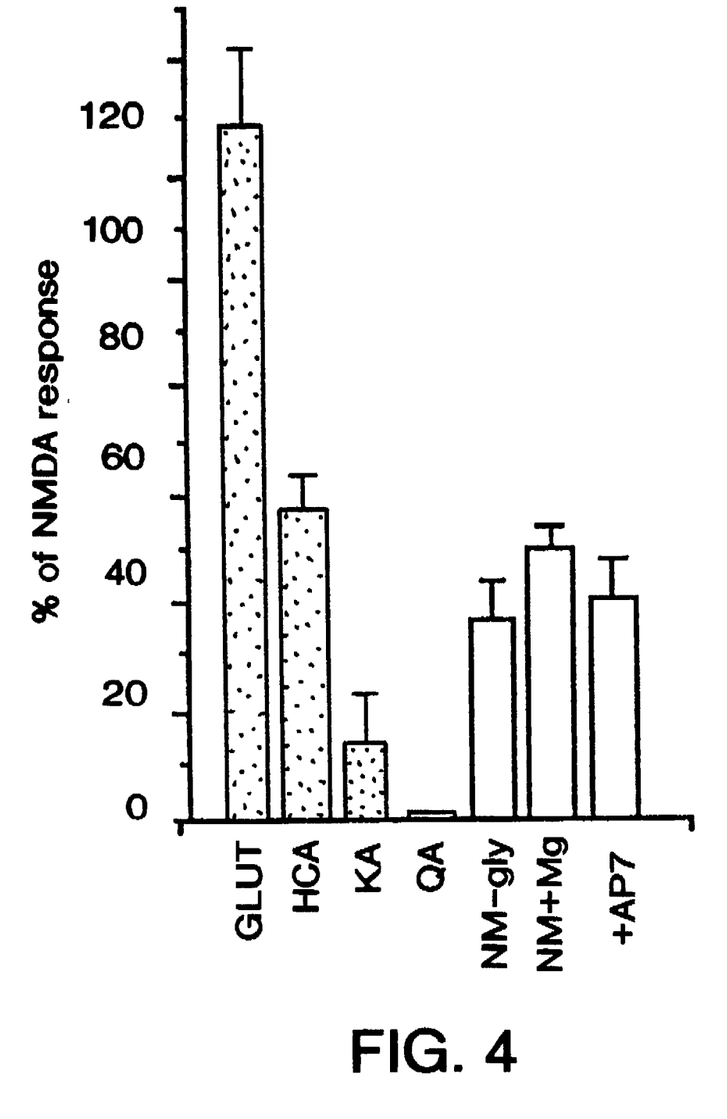
FIG. 4: Pharmacological and electrophysiological study of the GR33 polypeptide of 288 amino acids, SEQ ID No. 2. The results are expressed as % of the current induced by 200 μM NMDA alone. GLUT=glutamate; HCA=200 μM homocysteate; KA=300 mM kainate; QA=50 μM quisqualate; NM-gly=200 μM NMDA in the absence of glycine; NM+Mg=200 μM NMDA in the presence of 200 μM $Mg^{2+}$; AP7=200 μM NMDA in the presence of 10 μM AP7. Each point represents a mean of at least 5 measurements performed on different Xenopus eggs.

The eggs thereby obtained were then tested for the presence of functional NMDA receptors at their surface. For this purpose, the eggs were transferred to modified OR-2 medium lacking magnesium, of composition: 88 mM NaCl, 2.5 mM KCl, 1 mM $CaCl_2$, 10 mM HEPES buffer, pH 7.4 adjusted with sodium hydroxide. The different drugs (ligands or modulators) were applied by perfusion (10 ml/min) for 10–30 seconds under an applied potential difference of −80 or −90 mV. The results obtained are presented in FIG. 4. They show that:

the application of glutamate (0.1–1 mM) or of its agonist, NMDA (200 µM), induces an inward current, whereas other glutamate agonists including kainate (300 mM) and quisqualate (50 µM) have little or no effect. These results indicate that the injected eggs present at their surface glutamate receptors coupled to functional ion channels, of the NMDA type.

the response induced by NMDA (200 µM) is abolished when the medium does not contain glycine, or when the NMDA antagonists, AP5 or AP7, are applied (200 µM) simultaneously with NMDA. This result indicates that the response to NMDA of the injected eggs is pharmacologically comparable to that of a native NMDA receptor.

the response induced by NMDA (200 µM) is decreased when magnesium (200 µM) is added to the medium, or when there is an increase in the external calcium concentration (2.5 mM).

5. Search for Homologous Nucleotide Sequences and Polypeptides in Other Tissues The nucleotide sequence SEQ ID No. 1 was then used as probe for demonstrating homologous sequences on other tissues. For this purpose, two techniques were used:

Northern blot hybridization, in situ hybridization.

The tissues used to search for homologous sequences are the following ones of murine origin: cerebellum, cortex, striatum, hippocampus.

5.1. Search by Northern Blotting

Poly(A) mRNAs were prepared from the tissues mentioned above according to the guanidinium isothiocyanate technique described by Chirgwin et al. [Biochemistry 18 (1979) 5294], followed by passage through an oligo(dT)-cellulose column. These mRNAs were then fractionated on agarose gel and thereafter transferred onto nylon membranes (Hybond N+). The probe used for hybridization corresponds to the whole 1.7-kb cDNA described in Example 2 (SEQ ID No. 1), previously labelled with $^{32}$P according to the technique described by Maniatis et al. (see general cloning techniques). Hybridization with the different tissues was carried out under highly stringent conditions: hybridization at 42° C., 6×SSC, 50% formamide, 1×Denhardt's, rinsing at 65° C., 0.1×SSC, 1% SDS.

Figure 5:
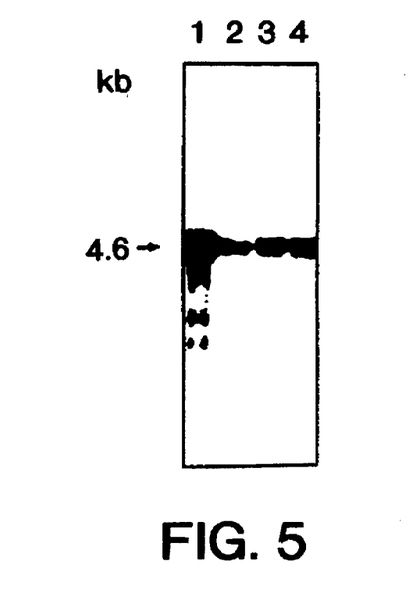
FIG. 5: Demonstration of homologous sequences by Northern blotting on poly(A) mRNA (1 μg) of cerebellum (lane 1), cortex (lane 2), striatum (lane 3) and hippocampus (lane 4). The probe used corresponds to the complete cDNA SEQ ID No. 1.

This study enabled homologous specific DNA fragments to be demonstrated in all the tissues studied (FIG. 5).

5.2. Search by In Situ Hybridization

In situ hybridization experiments were carried out on cryostat sections of rat brain according to the technique described by Hafen et al. [EMBO J. 2 (1983) 617]. The probe used for these experiments corresponds to the whole 1.7-kb cDNA described in Example 2 (SEQ ID No. 1) previously labelled by means of digoxigenin-labelled deoxyuridine triphosphate (dig-U, Boehringer Mannheim) according to the technique described by Dumas et al. [J. Neurosci. Res. 25 (1990) 569]. This non-radioactive labelling and also the detection of the hybrids were carried out by immunoenzymatic testing using anti-digoxigenin antibodies conjugated to alkaline phosphatase, which are visualized in the presence of a chromogenic substrate for the enzyme, 5-bromo-4-chloro-3-indolyl phosphate, and nitro blue tetrazolium salt, following the recommendations of the manufacturer (Boehringer Mannheim). Hybridization with the different tissues was carried out under highly stringent conditions: hybridization at 42° C., 6×SSC, 50% formamide, 1×Denhardt's, rinsing at 65° C., 0.1×SSC, 1% SDS.

This study enabled homologous sequences according to the invention to be demonstrated, in particular in Purkinje cells and in granular cells of the cerebellum, in pyramidal cells of the CA1 and CA3 regions of the hippocampus and in some regions of the cortex.

It is understood that the same experiments may be repeated using other tissues, and in particular tissues of human origin, and other probes. Moreover, the homologous sequences demonstrated in these experiments may naturally be isolated and/or amplified thereafter by standard techniques of molecular biology.

6. Use of Anti-GR33 Polypeptides Antibodies for Demonstrating Homologous Nucleotide Sequences and Polypeptides in Other Tissues Polyclonal anti-GR33 polypeptides antibodies were prepared and used for demonstrating homologous polypeptides on other tissues by Western blot experiments.

6.1. Preparation of Antibodies

A cDNA fragment containing the region coding for the GR33 polypeptide SEQ ID No. 1 described in Example 2 was generated by PCR by means of the following specific oligonucleotides:

TAATACGACTCACTATAGGATCCGACCCCGGCCTCCAGCA
(SEQ ID NO: 5)                                           (i)

GCAATTAACCCTCACTAAAGAATTC-
CCGATGTGTGGGGAGG (SEQ ID NO: 6)             (ii)

These oligonucleotides correspond to positions 124 and 1104, respectively, in the sequence SEQ ID No. 1.

The product of this amplification was then subcloned into the E. coli expression vector pGEX-2 [Smith and Johnston, Gene 67 (1988) 31] so as to permit its expression in the form of a fusion protein with glutathione S-transferase (GST-GR33). The fusion protein thereby produced was then purified and used as antigen for preparing antibodies in rabbits. For this purpose, rabbits were immunized with 50–100 µg of antigen in the presence of Freund's complete adjuvant. After 3 weeks, a further injection was carried out with 50 µg of antigen, but without Freund's complete adjuvant. After 2 injections, sera were collected and stored frozen.

6.2. Demonstration of Homologous Sequences

Synaptosomal membranes were prepared according to the technique described by Michaelis et al. [J. Neurochem. 42 (1984) 397] and solubilized in the presence of 0.5% sodium deoxycholate. Approximately 50 µg of proteins thereby obtained were subjected to an electrophoretic analyses on 10% SDS gel. The proteins were then transferred onto nitrocellulose and brought into contact with the antibodies prepared in 6.1. above. The bound antibodies were then visualized by means of the ECL detection system (Amersham).

Figure 6:
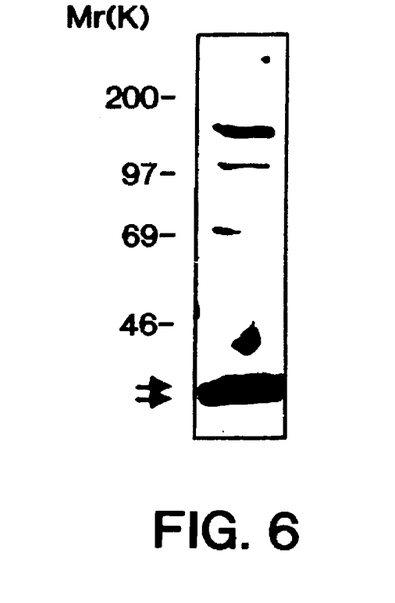
FIG. 6: Demonstration of homologous polypeptides by Western blotting on synaptosomal membranes.

As seen in FIG. 6, this study enabled different polypeptides comprising all or part of the peptide sequence SEQ ID No. 2 and having molecular weights of 35 kDa, 69–70 kDa, 97–98 kDa and 110 kDa approximately, to be demonstrated in synaptosomal membranes.

7. Isolation and Characterization of a Human Genomic Clone Coding for a GR33 Polypeptide This example describes the isolation and characterization of a human genomic clone coding from a GR33 polypeptide. This clone was obtained by screening a human library using radio labelled cDNA H500 as probe.

Figure 2:
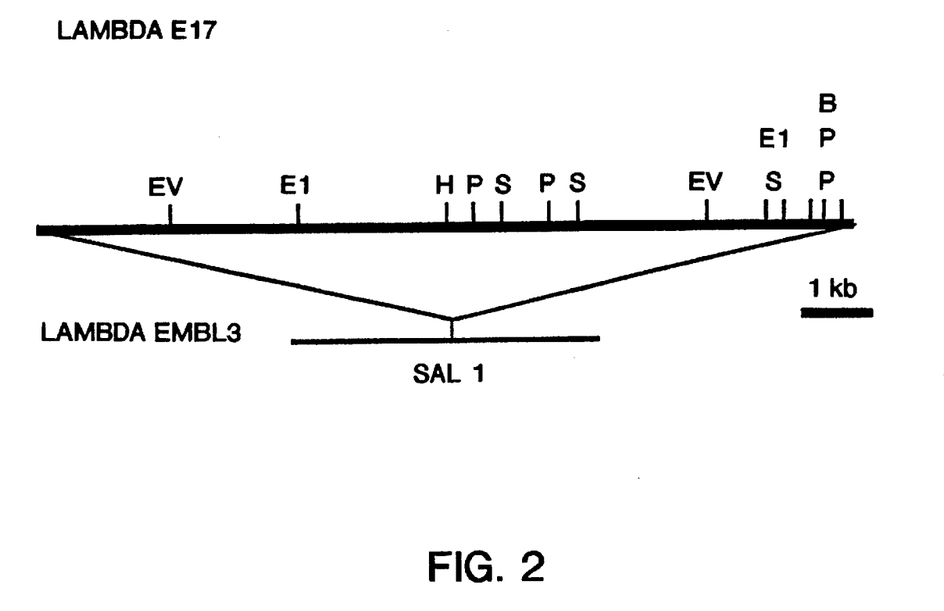
FIG. 2: Restriction map of the human genomic clone carrying a sequence homologous with the sequence SEQ ID No. 1. EV=EcoRV; EI=EcoR1; H=HindIII; P=PstI; S=SmaI; B=BamHI.

The human clone of FIG. 2 was obtained by screening a human genomic library constructed in the vector lambda EMBL3 (Clontech). This library contains approximately 13-kb genomic inserts inserted into the SalI site of the vector lambda EMBL3. This library was screened with cDNA H500 previously labelled with $^{32}$P by the "random priming" technique [Feinberg and Vogelstein, Analytical Biochemistry 132 (1984) 6]. Hybridization was carried out under the following highly stringent conditions: hybridization at 65° C., 3–4×SSC, 5×Denhardt's, rinsing at 65° C., 0.1×SSC, 1% SDS. Approximately 2×10$^5$ clones of the library were analysed in this way. One positive clone was isolated and purified. The plasmid thereby obtained (E17) carries an approximately 12-kb genomic insert, a restriction map of which is presented in FIG. 3. The sequence coding for the GR33 polypeptide is located in the 3' 6.5-kb HindIII-PstI fragment of plasmid E17.

We claim:

1. An isolated polypeptide comprising a sequence selected from the group consisting of:
   (a) SEQ ID No. 2,
   (b) SEQ ID No. 4, and
   (c) a fragment of (a) or (b) wherein said fragment has NMDA receptor activity.

2. A polypeptide according to claim 1, characterized in that it possesses the capacity to bind glutamate.

3. A polypeptide according to claim 2, characterized in that it possesses NMDA receptor activity.

4. A polypeptide according to claim 1, characterized in that it can be recognized by antibodies which recognize the complete peptide sequence SEQ ID No. 2.

5. A polypeptide according to claim 4, characterized in that it is selected from the group consisting of polypeptides having a molecular weight of 35 kDa, 69–70 kDa, 97–98 kDa and 110 kDa described in FIG. 6.

6. A polypeptide according to claim 1, characterized in that it comprises the sequence SEQ ID No. 2.

7. A polypeptide according to claim 1, characterized in that it comprises the sequence SEQ ID No. 4.

8. An recombinant nucleic acid encoding for a polypeptide, wherein said polypeptide comprises an amino acid sequence selected from the group consisting of;
   (a) SEQ ID NO: 2
   (b) SEQ ID NO: 4 and
   (c) a fragment of (a) or (b) wherein said fragment has NMDA receptor activity.

9. A nucleic acid according to claim 8, comprising a sequence selected from the group consisting of:
   (a) SEQ ID No. 1,
   (b) sequences which hybridize with (a) under highly stringent conditions, and
   (c) sequences derived from (a) and (b) as a result of the degeneracy of the genetic code.

10. A nucleic acid according to claim 8, comprising a sequence selected from the group consisting of:
    (a) SEQ ID No. 3,
    (b) sequences which hybridize with (a) under highly stringent conditions, and
    (c) sequences derived from (a) and (b) as a result of the degeneracy of the genetic code.

11. A nucleic acid according to claim 8, wherein said nucleic acid is placed under the control of signals permitting its expression in a host cell.

12. A recombinant cell comprising a nucleic acid according to claim 8.

13. A cell according to claim 12, selected from the group consisting of eukaryotic cells and prokaryotic cells.

14. A vector comprising the nucleic acid of claim 8.

15. A pharmaceutical composition comprising a vector according to claim 14.

16. An isolated nucleic acid encoding a polypeptide, wherein said polypeptide comprises an amino acid sequence selected from the group consisting of;
    (a) SEQ ID NO: 2
    (b) SEQ ID NO: 4 and
    (c) a fragment of (a) or (b) wherein said fragment has NMDA receptor activity; and
    wherein said nucleic acid is selected from the group consisting of genomic DNA, cDNA, RNA, hybrid nucleic acids, synthetic nucleic acids and semi-synthetic nucleic acids.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1200 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( i x ) FEATURE:
        ( A ) NAME/KEY: CDS
        ( B ) LOCATION: 211..1077

( x i ) SEQUENCE DESCRIPTION: SEQ ID NO:1:

```
ATTCCGGGCA  GCCTAGGCAG  AGCCAGTCGG  CCCAGGCCCC  TGTCTCTGCC  TGGCCTCAGC      60

TCCCCGCCCC  CCCGCCGCGC  ACCTTACCCG  CACATCCCTC  GGAGGTCTAG  CCGGGTGCCC     120

CCAGACCCCG  GCCTCCAGCA  CAGAGGCAAG  AGGCAGAGAG  CAGCAGCGGA  GGCGGGAGGA     180

CGAAGAAGGG  GAGGAGGAGC  CCGTCGCAGG  ATG  AAG  GAT  CGG  ACT  CAG  GAG  CTG      234
                                  Met  Lys  Asp  Arg  Thr  Gln  Glu  Leu
                                   1                5

CGG  AGT  GCA  AAA  GAC  AGT  GAC  GAT  GAA  GAG  GAA  GTG  GTT  CAT  GTG  GAT      282
Arg  Ser  Ala  Lys  Asp  Ser  Asp  Asp  Glu  Glu  Glu  Val  Val  His  Val  Asp
      10                  15                  20

CGA  GAC  CAC  TTT  ATG  GAT  GAG  TTC  TTT  GAG  CAG  GTG  GAA  GAG  ATC  CGA      330
Arg  Asp  His  Phe  Met  Asp  Glu  Phe  Phe  Glu  Gln  Val  Glu  Glu  Ile  Arg
 25                  30                  35                  40

GGC  TGC  ATC  GAG  AAA  CTG  TCC  GAG  GAT  GTG  GAG  CAA  GTG  AAG  AAA  CAG      378
Gly  Cys  Ile  Glu  Lys  Leu  Ser  Glu  Asp  Val  Glu  Gln  Val  Lys  Lys  Gln
                  45                  50                  55

CAC  AGT  GCC  ATT  CTT  GCT  GCC  CCC  AAC  CCC  GAT  GAG  AAG  ACT  AAA  CAG      426
His  Ser  Ala  Ile  Leu  Ala  Ala  Pro  Asn  Pro  Asp  Glu  Lys  Thr  Lys  Gln
              60                  65                  70

GAG  CTG  GAG  GAC  CTC  ACG  GCA  GAC  ATC  AAA  AAG  ACG  GCA  AAC  AAG  GTC      474
Glu  Leu  Glu  Asp  Leu  Thr  Ala  Asp  Ile  Lys  Lys  Thr  Ala  Asn  Lys  Val
              75                  80                  85

CGG  TCC  AAG  TTG  AAA  GCG  ATC  GAG  CAG  AGC  ATT  GAG  CAG  GAA  GAG  GGG      522
Arg  Ser  Lys  Leu  Lys  Ala  Ile  Glu  Gln  Ser  Ile  Glu  Gln  Glu  Glu  Gly
      90                  95                 100

TTG  AAT  CGT  TCT  TCT  GCA  GAC  CTG  CGT  ATC  CGT  AAG  ACC  CAG  CAC  TCC      570
Leu  Asn  Arg  Ser  Ser  Ala  Asp  Leu  Arg  Ile  Arg  Lys  Thr  Gln  His  Ser
105                 110                 115                 120

ACA  CTC  TCA  CGG  AAG  TTC  GTG  GAG  GTA  ATG  ACC  GAA  TAT  AAT  GCA  ACT      618
Thr  Leu  Ser  Arg  Lys  Phe  Val  Glu  Val  Met  Thr  Glu  Tyr  Asn  Ala  Thr
                 125                 130                 135

CAG  TCT  AAG  TAC  CGG  GAC  CGC  TGC  AAG  GAC  CGT  ATC  CAG  AGG  CAG  CTG      666
Gln  Ser  Lys  Tyr  Arg  Asp  Arg  Cys  Lys  Asp  Arg  Ile  Gln  Arg  Gln  Leu
                 140                 145                 150

GAG  ATC  ACT  GGC  AGG  ACT  ACT  ACC  AAC  GAA  GAG  CTG  GAA  GAC  ATG  TTG      714
Glu  Ile  Thr  Gly  Arg  Thr  Thr  Thr  Asn  Glu  Glu  Leu  Glu  Asp  Met  Leu
          155                 160                 165

GAA  AGC  GGG  AAG  CTG  GCC  ATC  TTC  ACG  GAC  GAC  ATC  AAA  ATG  GAC  TCG      762
```

-continued

| | | | | | | | | | | | | | | | |
|---|---|---|---|---|---|---|---|---|---|---|---|---|---|---|---|
| | Glu | Ser | Gly | Lys | Leu | Ala | Ile | Phe | Thr | Asp | Asp | Ile | Lys | Met | Asp Ser |
| | | 170 | | | | 175 | | | | | 180 | | | | |

| CAG | ATG | ACA | AAG | CAA | GCC | CTG | AAT | GAG | ATA | GAG | ACA | AGG | CAC | AAT | GAG | 810 |
|---|---|---|---|---|---|---|---|---|---|---|---|---|---|---|---|---|
| Gln | Met | Thr | Lys | Gln | Ala | Leu | Asn | Glu | Ile | Glu | Thr | Arg | His | Asn | Glu | |
| 185 | | | | 190 | | | | | 195 | | | | | 200 | | |

| ATC | ATC | AAA | CTG | GAA | ACC | AGC | ATC | CGA | GAG | CTG | CAC | GAC | ATG | TTT | GTG | 858 |
|---|---|---|---|---|---|---|---|---|---|---|---|---|---|---|---|---|
| Ile | Ile | Lys | Leu | Glu | Thr | Ser | Ile | Arg | Glu | Leu | His | Asp | Met | Phe | Val | |
| | | | | 205 | | | | | 210 | | | | | 215 | | |

| GAC | ATG | GCC | ATG | CTC | GTG | GAG | AGC | CAG | GGT | GAG | ATG | ATC | GAC | CGA | ATT | 906 |
|---|---|---|---|---|---|---|---|---|---|---|---|---|---|---|---|---|
| Asp | Met | Ala | Met | Leu | Val | Glu | Ser | Gln | Gly | Glu | Met | Ile | Asp | Arg | Ile | |
| | | | 220 | | | | | 225 | | | | | 230 | | | |

| GAG | TAC | AAT | GTG | GAA | CAT | TCT | GTG | GAC | TAC | GTG | GAG | CGA | GCC | GTG | TCC | 954 |
|---|---|---|---|---|---|---|---|---|---|---|---|---|---|---|---|---|
| Glu | Tyr | Asn | Val | Glu | His | Ser | Val | Asp | Tyr | Val | Glu | Arg | Ala | Val | Ser | |
| | | 235 | | | | | 240 | | | | | 245 | | | | |

| GAC | ACC | AAG | AAA | GCT | GTG | AAA | TAT | CAG | AGC | AAG | GCC | AGG | AGG | AAG | AAA | 1002 |
|---|---|---|---|---|---|---|---|---|---|---|---|---|---|---|---|---|
| Asp | Thr | Lys | Lys | Ala | Val | Lys | Tyr | Gln | Ser | Lys | Ala | Arg | Arg | Lys | Lys | |
| | 250 | | | | | 255 | | | | | 260 | | | | | |

| ATT | ATG | ATC | ATC | ATT | TGC | TGT | GTG | GTG | CTG | GGG | GTG | GTC | TTG | GCG | TCA | 1050 |
|---|---|---|---|---|---|---|---|---|---|---|---|---|---|---|---|---|
| Ile | Met | Ile | Ile | Ile | Cys | Cys | Val | Val | Leu | Gly | Val | Val | Leu | Ala | Ser | |
| 265 | | | | | 270 | | | | | 275 | | | | | 280 | |

| TCT | ATT | GGG | GGG | ACA | CTG | GGC | TTG | TAGGCCCCTA | CCCTTCTCTT | CCCCAGGACC | 1104 |
|---|---|---|---|---|---|---|---|---|---|---|---|
| Ser | Ile | Gly | Gly | Thr | Leu | Gly | Leu | | | | |
| | | | | 285 | | | | | | | |

CTCCCCACAC ATCGGGAGCA ATACCCCCAC CACCCTTTCA CTCTTTCCCC TGCTCCAAGC    1164

TCACTCCCAA AACAGACCCA GGCAGTTCCA GCCTCT    1200

( 2 ) INFORMATION FOR SEQ ID NO:2:

( i ) SEQUENCE CHARACTERISTICS:
        ( A ) LENGTH: 288 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Lys | Asp | Arg | Thr | Gln | Glu | Leu | Arg | Ser | Ala | Lys | Asp | Ser | Asp | Asp |
| 1 | | | | 5 | | | | | 10 | | | | | 15 | |
| Glu | Glu | Glu | Val | Val | His | Val | Asp | Arg | Asp | His | Phe | Met | Asp | Glu | Phe |
| | | | 20 | | | | | 25 | | | | | 30 | | |
| Phe | Glu | Gln | Val | Glu | Glu | Ile | Arg | Gly | Cys | Ile | Glu | Lys | Leu | Ser | Glu |
| | | 35 | | | | | 40 | | | | | 45 | | | |
| Asp | Val | Glu | Gln | Val | Lys | Lys | Gln | His | Ser | Ala | Ile | Leu | Ala | Ala | Pro |
| | 50 | | | | | 55 | | | | | 60 | | | | |
| Asn | Pro | Asp | Glu | Lys | Thr | Lys | Gln | Glu | Leu | Glu | Asp | Leu | Thr | Ala | Asp |
| 65 | | | | | 70 | | | | | 75 | | | | | 80 |
| Ile | Lys | Lys | Thr | Ala | Asn | Lys | Val | Arg | Ser | Lys | Leu | Lys | Ala | Ile | Glu |
| | | | | 85 | | | | | 90 | | | | | 95 | |
| Gln | Ser | Ile | Glu | Gln | Glu | Glu | Gly | Leu | Asn | Arg | Ser | Ser | Ala | Asp | Leu |
| | | | 100 | | | | | 105 | | | | | 110 | | |
| Arg | Ile | Arg | Lys | Thr | Gln | His | Ser | Thr | Leu | Ser | Arg | Lys | Phe | Val | Glu |
| | | 115 | | | | | 120 | | | | | 125 | | | |
| Val | Met | Thr | Glu | Tyr | Asn | Ala | Thr | Gln | Ser | Lys | Tyr | Arg | Asp | Arg | Cys |
| | 130 | | | | | 135 | | | | | 140 | | | | |
| Lys | Asp | Arg | Ile | Gln | Arg | Gln | Leu | Glu | Ile | Thr | Gly | Arg | Thr | Thr | Thr |
| 145 | | | | | 150 | | | | | 155 | | | | | 160 |
| Asn | Glu | Glu | Leu | Glu | Asp | Met | Leu | Glu | Ser | Gly | Lys | Leu | Ala | Ile | Phe |
| | | | | 165 | | | | | 170 | | | | | 175 | |

```
Thr  Asp  Asp  Ile  Lys  Met  Asp  Ser  Gln  Met  Thr  Lys  Gln  Ala  Leu  Asn
               180                      185                      190

Glu  Ile  Glu  Thr  Arg  His  Asn  Glu  Ile  Ile  Lys  Leu  Glu  Thr  Ser  Ile
          195                      200                      205

Arg  Glu  Leu  His  Asp  Met  Phe  Val  Asp  Met  Ala  Met  Leu  Val  Glu  Ser
     210                      215                      220

Gln  Gly  Glu  Met  Ile  Asp  Arg  Ile  Glu  Tyr  Asn  Val  Glu  His  Ser  Val
225                           230                 235                      240

Asp  Tyr  Val  Glu  Arg  Ala  Val  Ser  Asp  Thr  Lys  Lys  Ala  Val  Lys  Tyr
                    245                      250                      255

Gln  Ser  Lys  Ala  Arg  Arg  Lys  Lys  Ile  Met  Ile  Ile  Ile  Cys  Cys  Val
               260                      265                      270

Val  Leu  Gly  Val  Val  Leu  Ala  Ser  Ser  Ile  Gly  Gly  Thr  Leu  Gly  Leu
          275                      280                      285
```

( 2 ) INFORMATION FOR SEQ ID NO:3:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Homo sapiens     ( i x ) FEATURE:
        ( A ) NAME/KEY: CDS
        ( B ) LOCATION: 2..475

( x i ) SEQUENCE DESCRIPTION: SEQ ID NO:3:

```
G  TTC  TTT  GAA  CAG  GTG  GAA  GAG  ATC  CGA  GGC  TGC  ATT  GAG  AAA  CTG         46
   Phe  Phe  Glu  Gln  Val  Glu  Glu  Ile  Arg  Gly  Cys  Ile  Glu  Lys  Leu
   1              5                        10                       15

TCG  GAG  GAT  GTG  GAG  CAG  GTG  AAA  AAA  CAG  CAT  AGC  GCC  ATC  CTG  GCC       94
Ser  Glu  Asp  Val  Glu  Gln  Val  Lys  Lys  Gln  His  Ser  Ala  Ile  Leu  Ala
                    20                       25                       30

GCA  CCC  AAC  CCA  GAT  GAG  AAG  ACC  AAA  CAG  GAG  CTG  GAG  GAT  CTC  ACT      142
Ala  Pro  Asn  Pro  Asp  Glu  Lys  Thr  Lys  Gln  Glu  Leu  Glu  Asp  Leu  Thr
               35                       40                       45

GCA  GAC  ATC  AAG  AAG  ACG  GCC  AAC  AAG  GTT  CGG  TCC  AAA  TTG  AAA  GCG      190
Ala  Asp  Ile  Lys  Lys  Thr  Ala  Asn  Lys  Val  Arg  Ser  Lys  Leu  Lys  Ala
          50                       55                       60

ATC  GAG  CAA  AGC  ATT  GAA  CAG  GAG  GAG  GGG  CTG  AAC  CGT  TCC  TCC  GCG      238
Ile  Glu  Gln  Ser  Ile  Glu  Gln  Glu  Glu  Gly  Leu  Asn  Arg  Ser  Ser  Ala
     65                       70                       75

GAC  CTG  CGC  ATC  CGC  AAG  ACC  CAG  CAC  TCC  ACA  CTG  TCC  CGG  AAG  TTC      286
Asp  Leu  Arg  Ile  Arg  Lys  Thr  Gln  His  Ser  Thr  Leu  Ser  Arg  Lys  Phe
80                       85                       90                       95

GTG  GAG  GTA  ATG  ACC  GAA  TAT  AAC  GCG  ACC  CAG  TCC  AAG  TAC  CGG  GAC      334
Val  Glu  Val  Met  Thr  Glu  Tyr  Asn  Ala  Thr  Gln  Ser  Lys  Tyr  Arg  Asp
                    100                      105                      110

CGC  TGC  AAG  GAC  CGG  ATC  CAG  CGG  CAA  CTG  GAG  ATC  ACT  GGA  AGG  ACC      382
Arg  Cys  Lys  Asp  Arg  Ile  Gln  Arg  Gln  Leu  Glu  Ile  Thr  Gly  Arg  Thr
               115                      120                      125

ACC  ACC  AAC  GAA  GAA  CTG  GAA  GAC  ATG  CTG  GAG  AGC  GGG  AAG  CTG  GCC      430
Thr  Thr  Asn  Glu  Glu  Leu  Glu  Asp  Met  Leu  Glu  Ser  Gly  Lys  Leu  Ala
```

```
                  130                        135                         140
ATC  TTC  ACA  GAT  GAC  ATC  AAA  ATG  GAC  TCA  CAG  ATG  ACG  AAA  CAG         475
Ile  Phe  Thr  Asp  Asp  Ile  Lys  Met  Asp  Ser  Gln  Met  Thr  Lys  Gln
     145                      150                      155

GC                                                                                477
```

( 2 ) INFORMATION FOR SEQ ID NO:4:

( i ) SEQUENCE CHARACTERISTICS:
        ( A ) LENGTH: 158 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

```
Phe  Phe  Glu  Gln  Val  Glu  Glu  Ile  Arg  Gly  Cys  Ile  Glu  Lys  Leu  Ser
 1                  5                        10                       15

Glu  Asp  Val  Glu  Gln  Val  Lys  Lys  Gln  His  Ser  Ala  Ile  Leu  Ala  Ala
               20                       25                       30

Pro  Asn  Pro  Asp  Glu  Lys  Thr  Lys  Gln  Glu  Leu  Glu  Asp  Leu  Thr  Ala
          35                       40                       45

Asp  Ile  Lys  Lys  Thr  Ala  Asn  Lys  Val  Arg  Ser  Lys  Leu  Lys  Ala  Ile
     50                       55                       60

Glu  Gln  Ser  Ile  Glu  Gln  Glu  Glu  Gly  Leu  Asn  Arg  Ser  Ser  Ala  Asp
65                       70                       75                       80

Leu  Arg  Ile  Arg  Lys  Thr  Gln  His  Ser  Thr  Leu  Ser  Arg  Lys  Phe  Val
               85                       90                       95

Glu  Val  Met  Thr  Glu  Tyr  Asn  Ala  Thr  Gln  Ser  Lys  Tyr  Arg  Asp  Arg
               100                      105                      110

Cys  Lys  Asp  Arg  Ile  Gln  Arg  Gln  Leu  Glu  Ile  Thr  Gly  Arg  Thr  Thr
          115                      120                      125

Thr  Asn  Glu  Glu  Leu  Glu  Asp  Met  Leu  Glu  Ser  Gly  Lys  Leu  Ala  Ile
     130                      135                      140

Phe  Thr  Asp  Asp  Ile  Lys  Met  Asp  Ser  Gln  Met  Thr  Lys  Gln
145                      150                      155
```

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: other nucleic acid     ( x i ) SEQUENCE DESCRIPTION: SEQ ID NO:5:

```
TAATACGACT  CACTATAGGA  TCCGACCCCG  GCCTCCAGCA                                     40
```

( 2 ) INFORMATION FOR SEQ ID NO:6:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: other nucleic acid     ( x i ) SEQUENCE DESCRIPTION: SEQ ID NO:6:

```
GCAATTAACC  CTCACTAAAG  AATTCCGAT  GTGTGGGGAG  G                                   41
```